United States Patent [19]
Audousset

[11] Patent Number: 6,001,136
[45] Date of Patent: Dec. 14, 1999

[54] COMPOSITIONS FOR THE OXIDATION DYEING OF KERATIN FIBRES AND DYEING PROCESS

[75] Inventor: Marie-Pascale Audousset, Asnieres, France

[73] Assignee: L'Oreal, France

[21] Appl. No.: 09/288,968

[22] Filed: Apr. 9, 1999

Related U.S. Application Data

[63] Continuation of application No. 08/896,632, Jul. 18, 1997, abandoned.

[30] Foreign Application Priority Data

Jul. 19, 1996 [FR] France .................................. 96-09109

[51] Int. Cl.⁶ .................................................... A61K 7/13
[52] U.S. Cl. .................................................... 8/412
[58] Field of Search .............................. 8/406, 408, 410, 8/412, 416, 421

[56] References Cited

U.S. PATENT DOCUMENTS

| | | | |
|---|---|---|---|
| 4,212,645 | 7/1980 | Leon et al. .................................. | 8/406 |
| 4,330,292 | 5/1982 | Bugaut et al. .............................. | 8/411 |
| 4,333,730 | 6/1982 | Bugaut et al. .............................. | 8/408 |
| 4,511,360 | 4/1985 | Monnais et al. ............................ | 8/408 |
| 4,863,481 | 9/1989 | Monnais et al. ............................ | 8/408 |
| 4,875,902 | 10/1989 | Grollier et al. ............................. | 8/408 |
| 5,443,596 | 8/1995 | Junino et al. ............................... | 8/408 |
| 5,514,188 | 5/1996 | Cotteret et al. ............................. | 8/410 |
| 5,518,505 | 5/1996 | Cotteret ...................................... | 8/408 |
| 5,518,506 | 5/1996 | Cotteret et al. ............................. | 8/410 |
| 5,567,421 | 10/1996 | Cotteret et al. ............................. | 8/412 |
| 5,578,087 | 11/1996 | Audousset et al. ......................... | 8/408 |
| 5,693,101 | 12/1997 | Audousset et al. ......................... | 8/408 |
| 5,863,300 | 1/1999 | Audousset et al. ......................... | 8/411 |

FOREIGN PATENT DOCUMENTS

| | | |
|---|---|---|
| 0 634 163 | 1/1995 | European Pat. Off. . |
| 0 634 164 | 1/1995 | European Pat. Off. . |
| 0 662 317 | 7/1995 | European Pat. Off. . |
| 0 728 465 | 8/1996 | European Pat. Off. . |
| 2 677 649 | 12/1992 | France . |

OTHER PUBLICATIONS

English Derwent Abstract of EP 0 728 465, Aug. 1996.
English Derwent Abstract of EP 0 634 164, Jan. 1995.
English Derwent Abstract of EP 0 662 317, Jul. 1995.
English Derwent Abstract of EP 0 634 163, Jan. 1995.
English Derwent Abstract of FR 2 677 649, Dec. 1992.
Venkataraman et al., The Chemistry of Synthetic Dyes, vol. V, p. 481, (1971), (No month available).

*Primary Examiner*—Caroline D. Liott
*Attorney, Agent, or Firm*—Finnegan, Henderson, Farabow, Garrett & Dunner, L.L.P.

[57] ABSTRACT

A composition for the oxidation dyeing of keratin fibers, in particular of human keratin fibers such as the hair, preferably comprising 2-n-propyl-para-phenylenediamine, in combination with at least one meta-aminophenol in a meta-aminophenol/2-n-propyl-para-phenylenediamine molar ratio of less than or equal to 10, as well as to the dyeing process using this composition.

24 Claims, No Drawings

COMPOSITIONS FOR THE OXIDATION DYEING OF KERATIN FIBRES AND DYEING PROCESS

This is a continuation of application Ser. No. 08/896,632, filed Jul. 18, 1997, now abandoned.

The invention relates to a composition for the oxidation dyeing of keratin fibres, in particular of human keratin fibres such as the hair, comprising 2-n-propyl-para-phenylenediamine, in combination with at least one meta-aminophenol in a meta-aminophenol/2-n-propyl-para-phenylenediamine molar ratio of less than or equal to 10:1, as well as to the dyeing process using this composition.

It is known to dye keratin fibres, and in particular human hair, with dye compositions containing oxidation dye precursors, in particular ortho or para-phenylenediamines, or ortho- or para-aminophenols which are generally referred to as oxidation bases. The oxidation dye precursors, or oxidation bases, are coloudess or weakly coloured compounds which, when combined with oxidizing products, may give rise to coloured compounds and dyes by a process of oxidative condensation.

It is also known that the shades obtained with these oxidation bases may be varied by combining them with couplers or coloration modifiers, it being possible for the latter to be chosen in particular from aromatic meta-diamines, meta-aminophenols and meta-diphenols.

The variety of molecules used as oxidation bases and couplers makes it possible to obtain a wide range of colours.

The so-called "permanent" coloration obtained by means of these oxidation dyes seeks to satisfy a certain number of requirements. Thus, it is desired to have no toxicological drawbacks and to allow shades of the desired intensity to be obtained and to have good staying power with respect to external agents (light, inclement weather, washing, permanent-waving, perspiration and rubbing).

It is also desired that the dyes allow white hairs to be covered and, lastly, to be as unselective as possible, that is to say to allow the smallest possible differences in coloration to be produced over the entire length of the same keratin fibre, which may indeed be differently sensitized (i.e. damaged) between its tip and its root.

Compositions for the oxidation dyeing of keratin fibres containing certain couplers of meta-aminophenol type, in combination with at least one oxidation dye precursor of para-phenylenediamine type or derivatives, have already been proposed. However, the colorations obtained with these compositions are not entirely satisfactory, in particular regarding the staying power of these colorations with respect to the various attacking factors to which the hair may be subjected and, in particular, to shampoos.

Compositions for the oxidation dyeing of keratin fibres containing, in particular, 2-n-propyl-para-phenylenediamine as oxidation base in combination with 2-methyl-5-N-($\beta$-hydroxyethyl)aminophenol as coupler, in a 2-methyl-5-N-($\beta$-hydroxyethyl)aminophenol/2-n-propyl-para-phenylenediamine molar ratio which is markedly greater than 10, have also already been proposed, in particular in patent application EP-A-0,634,163. However, these compositions are not entirely satisfactory, in particular regarding the intensity of the colorations obtained.

The aim of the present invention is to propose novel compositions for the oxidation dyeing of keratin fibres, and in particular of human keratin fibres such as the hair, which have very good dyeing properties.

Thus, the inventor has just discovered that it is possible to obtain novel dyes of particularly good staying power, which give rise to intense colorations, by combining:

at least one oxidation base selected from 2-n-propyl-para-phenylenediamine and acid addition salts thereof, and at least one coupler selected from meta-aminophenol of formula (I) defined below and acid addition salts thereof, it being understood that the meta-aminophenol of formula (I)/2-n-propyl-para-phenylenediamine molar ratio is less than or equal to 10:1.

This discovery forms the basis of the present invention.

The first subject of the invention is thus a composition for the oxidation dyeing of keratin fibres, and in particular of human keratin fibres such as the hair, characterized in that it comprises, in an appropriate medium for dyeing:

at least one oxidation base selected from 2-n-propyl-para-phenylenediamine and acid addition salts thereof, at least one coupler selected from the meta-aminophenols of formula (I) below, and acid addition salts thereof:

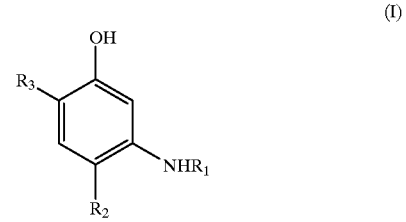

(I)

wherein:

$R_1$ represents a hydrogen atom or a $C_1$–$C_4$ alkyl, $C_1$–$C_4$ monohydroxyalkyl or $C_2$–$C_4$ polyhydroxyalkyl radical, $R_2$ represents a hydrogen atom, a $C_1$–$C_4$ alkyl or $C_1$–$C_4$ alkoxy radical or a halogen atom selected from chlorine, bromine and fluorine, $R_3$ represents a hydrogen atom or a $C_1$–$C_4$ alkyl, $C_1$–$C_4$ alkoxy, $C_1$–$C_4$ monohydroxyalkyl, $C_2$–$C_4$ polyhydroxyalkyl, $C_1$–$C_4$ monohydroxyalkoxy or $C_2$–$C_4$ polyhydroxyalkoxy radical, wherein the meta-aminophenol of formula (I)/2-n-propyl-para-phenylenediamine molar ratio is less than or equal to 10:1.

As demonstrated by the examples below, the colorations obtained with the above compositions are of good dyeing power and have excellent properties of staying power both with respect to atmospheric agents such as light and bad weather and with respect to perspiration and the various treatments to which the hair may be subjected (shampooing, permanent-waving). These properties are particularly noteworthy, especially regarding the staying power of the colorations obtained with respect to shampooing.

The subject of the invention is also a process for the oxidation dyeing of keratin fibres using this composition.

According to a preferred embodiment of the invention, the meta-aminophenol of formula (I)/2-n-propyl-para-phenylenediamine molar ratio is less than or equal to 5:1.

The addition salts with an acid which may be used in the context of the dye compositions of the invention may be chosen in particular from hydrochlorides, hydrobromides, sulphates and tartrates.

Among the meta-aminophenols of formula (I) above which may be mentioned more particularly are meta-aminophenol, 5-amino-2-methoxyphenol, 5-amino-2-($\beta$-hydroxyethyloxy)phenol, 5-amino-2-methylphenol, 5-N-($\beta$-hydroxyethyl)amino-2-methylphenol, 5-N-($\beta$-hydroxyethyl)amino-4-methoxy-2-methylphenol, 5-amino- 4-methoxy-2-methylphenol, 5-amino-4-chloro-2-methylphenol, 5-amino-2,4-dimethoxyphenol and 5-(γ-hydroxypropylamino)-2-methylphenol, and the addition salts thereof with an acid.

The 2-n-propyl-para-phenylenediamine and/or the addition salt or salts of this compound with an acid preferably represent from 0.0005 to 10% by weight approximately relative to the total weight of the dye composition, and even more preferably from 0.05 to 7% by weight approximately.

The meta-aminophenol(s) of formula (I) in accordance with the invention preferably represent from 0.0001 to 5% by weight approximately relative to the total weight of the dye composition, and even more preferably from 0.005 to 3% by weight approximately.

The appropriate medium for the dyeing (or the support) generally comprises water or a mixture of water and at least one organic solvent to solubilize the compounds which would not be sufficiently soluble in water. Organic solvents which may be mentioned, for example, are $C_1$–$C_4$ lower alkanols such as ethanol and isopropanol; glycerol; glycols and glycol ethers such as 2-butoxyethanol, propylene glycol, monoethyl ether and diethylene glycol monomethyl ether as well as aromatic alcohols such as benzyl alcohol or phenoxyethanol, similar products and mixtures thereof.

The solvents may be present in proportions preferably approximately from 1 to 40% by weight relative to the total weight of the dye composition, and even more preferably approximately from 5 to 30% by weight.

The pH of the dye composition as defined above generally ranges approximately from 5 to 12. It may be adjusted to the desired value using acidifying or basifying agents usually used in the dyeing of keratin fibres.

Among the acidifying agents which may be mentioned, by way of example, are inorganic or organic acids such as hydrochloric acid, orthophosphoric acid, carboxylic acids such as tartaric acid, citric acid, lactic acid and sulphonic acids.

Among the basifying agents which may be mentioned, by way of example, are aqueous ammonia, alkaline carbonates, alkanolamines such as mono-, di- and triethanolamines and derivatives thereof, sodium hydroxide or potassium hydroxide and the compounds of formula (II) below:

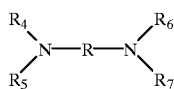

(II)

in which R is a propylene residue optionally substituted with a hydroxyl group or a $C_1$–$C_4$ alkyl radical; $R_4$, $R_5$, $R_6$ and $R_7$, which may be identical or different, represent a hydrogen atom or a $C_1$–$C_4$ alkyl or $C_1$–$C_4$ hydroxyalkyl radical.

The dye composition in accordance with the invention may also contain, in addition to the dyes defined above, other oxidation bases and/or other couplers and/or other direct dyes, in particular in order to modify the shades or to enrich them with glints.

The dye composition according to the invention may also include various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifying agents.

Obviously, a person skilled in the art will take care to select the optional complementary compound(s) mentioned above, such that the advantageous properties intrinsically associated with the dye composition in accordance with the invention are not, or are not substantially, adversely affected by the addition or additions envisaged.

The dye composition according to the invention may be in various forms, such as in the form of liquids, creams, gels or any other form which is suitable for dyeing keratin fibres, and in particular human hair.

The subject of the invention is also a process for dyeing keratin fibres, and in particular human keratin fibres such as the hair, using the dye composition as defined above.

According to this process, the dye composition as defined above is applied to the fibres to be dyed, the colour being developed at acidic, neutral or alkaline pH using an oxidizing agent which is added only at the time of use to the dye composition or which is present in an oxidizing composition that is applied simultaneously or sequentially in a separate manner.

According to a preferred embodiment of the invention, the resulting pH of the mixture of the dye composition and of the oxidizing composition ranges approximately from 5 to 12.

According to a particularly preferred embodiment of the dyeing process according to the invention, the dye composition described above is mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for preferably 3 to 40 minutes approximately, more preferably 5 to 30 minutes approximately, after which the fibres are rinsed, washed with shampoo, rinsed again and dried.

The oxidizing agent present in the oxidizing composition as defined above may be chosen from the oxidizing agents conventionally used for the oxidation dyeing of keratin fibres, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resulting composition applied to the keratin fibres preferably ranges approximately from 2 to 12 and even more preferably from 5 to 11. It is adjusted to the desired value using acidifying or basifying agents usually used in the dyeing of keratin fibres and as are defined above.

The oxidizing composition as defined above may also include various adjuvants used conventionally in compositions for dyeing the hair and as are defined above.

The composition which is finally applied to the keratin fibres may be in various forms, such as in the form of liquids, creams, gels or any other form which is suitable for dyeing keratin fibres, and in particular human hair.

Another subject of the invention is a multi-compartment device for dyeing or dyeing "kit" or any other multi-compartment packaging system a first compartment of which contains the dye composition as defined above and a second compartment of which contains the oxidizing composition as defined above. These devices may be equipped with a means which makes it possible to deliver the desired mixture onto the hair, such as the devices described in patent FR-2,586,913 in the name of L'Oréal, the disclosure of which is specifically incorporated by reference herein.

The examples which follow are intended to illustrate the invention without, however, limiting the scope thereof.

EXAMPLES

Comparative Examples 1 and 2

The following dye compositions were prepared (contents in grams):

| EXAMPLE | 1 | 2(*) |
|---|---|---|
| 2-n-Propyl-para-phenylenediamine dihydrochloride (oxidation base) | 0.669 | — |
| 2,6-Dimethyl-para-phenylenediamine dihydrochloride (oxidation base) | — | 0.627 |
| 2-Methyl-5-aminophenol (coupler) | 0.369 | 0.369 |
| Common dye support () | () | (**) |
| Water qs | 100 g | 100 g |
| (*): example not forming part of the invention | | |
| (**) common dye support: | | |
| Oleyl alcohol polyglycerolated with 2 mol of glycerol | 4.0 g | |
| Oleyl alcohol polyglycerolated with 4 mol of glycerol, containing 78% of active material (AM) | 5.69 g AM | |
| Oleic acid | 3.0 g | |
| Oleylamine containing 2 mol of ethylene oxide, sold under the trade name Ethomeen O12 by the company Akzo | 7.0 g | |
| Diethylaminopropyl laurylamino succinimate, sodium salt, containing 55% AM | 3.0 g AM | |
| Oleyl alcohol | 5.0 g | |
| Oleic acid diethanolamide | 12.0 g | |
| Propylene glycol | 3.5 g | |
| Ethyl alcohol | 7.0 g | |
| Dipropylene glycol | 0.5 g | |
| Propylene glycol monomethyl ether | 9.0 g | |
| Sodium metabisulphite in aqueous solution, containing 35% AM | 0.455 g AM | |
| Ammonium acetate | 0.8 g | |
| Antioxidant, sequestering agent | qs | |
| Fragrance, preserving agent | qs | |
| Aqueous ammonia containing 20% $NH_3$ | 10.0 g | |

It is important to note that each dye composition contains the same molar amount of oxidation base, namely $3 \times 10^{-3}$ mol.

Each dye composition was mixed, at the time of use, with an equal amount of an oxidizing composition of 20-volumes aqueous hydrogen peroxide solution (6% by weight) having a pH of about 3.

Each mixture obtained had a pH of about 10.2 and was applied for 30 minutes to locks of permanent-waved grey hair. The locks of hair were then rinsed, washed with a standard shampoo and then dried.

The colour of the locks was then evaluated in the Munsell system using a Minolta CM 2002 colorimeter.

According to the Munsell notation, a colour is defined by the expression HV/C in which the three parameters respectively denote the shade or Hue (H), the intensity or Value (V) and the purity or Chromaticity (C), the oblique line in this expression simply being a convention and not indicating a ratio.

The locks of hair thus dyed were then subjected to a test of resistance to washing (Ahiba-Texomat machine).

To do this, the locks of hair were placed in a basket which was immersed in a solution of a standard shampoo. The basket was subjected to a to-and-fro motion of variable frequency as well as to a rotational motion, which reproduced the action of manual rubbing, thereby causing the formation of foam.

After a test time of 3 minutes, the locks were removed and then rinsed and dried. The dyed locks were subjected to 6 consecutive shampooing tests.

The colour of the locks was then evaluated again in the Munsell system using a Minolta CM 2002 calorimeter.

The difference between the colour of the lock before the shampooings and the colour of the lock after the shampooings was calculated by applying the Nickerson formula:

$$\Delta E = 0.4 Co \Delta H + 6 \Delta V + 3 \Delta C,$$

as described, for example, in "Couleur, Industrie et Technique"; pages 14–17; vol. No. 5; 1978.

In this formula, $\Delta E$ represents the difference in colour between two locks, $\Delta H$, $\Delta V$ and $\Delta C$ represent the variation in absolute value of the parameters H, V and C, and Co represents the purity of the lock relative to which it is desired to evaluate the colour difference.

The results are given in the table below:

| EX-AMPLE | Color of the hair before the shampooings | Color of the hair after the shampooings | Degradation of the color | | | |
|---|---|---|---|---|---|---|
| | | | $\Delta H$ | $\Delta V$ | $\Delta C$ | $\Delta E$ |
| 1 | 3.4 RP 2.5/2.8 | 5 RP 3.3/2.2 | 1.6 | 0.8 | 0.6 | 8.4 |
| 2(*) | 6 RP 2.6/2.4 | 1.1 YR 4.2/1.2 | 15.1 | 1.6 | 1.2 | 27.7 |

(*) : example not forming part of the invention.

These results show that composition 1 containing the combination of 2-n-propyl-para-phenylenediamine and 2-methyl-5-amino phenol in accordance with the invention leads to a coloration which has a much better staying power with regard to perspiration than the composition 2 containing an oxidation base which does not form part of the invention, namely 2,6-dimethyl-para-phenylenediamine and as described, for example, in European patent application EP-A-0,634,164.

Comparative Examples 3 and 4

The following dye compositions were prepared (contents in moles):

| EXAMPLE | 3 | 4(*) |
|---|---|---|
| 2-n-Propyl-para-phenylenediamine dihydrochloride (oxidation base) | $4.79 \times 10^{-4}$ | $4.48 \times 10^{-5}$ |
| 2-Methyl-5-N-(β-hydroxyethyl)aminophenol (coupler) | $4.79 \times 10^{-3}$ | $4.79 \times 10^{-3}$ |
| Coupler/oxidation base molar ratio | 10 | 107 |
| Common dye support () | () | (**) |
| Water qs | 100 g | 100 g |

(*): example not forming part of the invention
(**) common dye support:

Each dye composition was mixed, at the time of use, with an equal amount of an oxidizing composition of 20-volumes aqueous hydrogen peroxide solution (6% by weight) having a pH of about 3.

Each mixture obtained had a pH of about 10.2 and was applied to locks of natural grey hair containing 90% white hairs according to the dyeing process described above for Examples 1 and 2.

The colour of the locks was evaluated in the Munsell system, before and after dyeing, using a Minolta CM 2002 colorimeter.

The difference $\Delta E$ between the colour of the lock before dyeing and the colour of the lock after dyeing was calculated by applying the Nickerson formula, and reflects the intensity of the coloration obtained.

The results are given in the table below:

| EX-AMPLE | Color of the hair before dyeing | Color of the hair after dyeing | Increase in coloration | | | |
|---|---|---|---|---|---|---|
| | | | ΔH | ΔV | ΔC | ΔE |
| 3 | 3.8 Y 5.5/1.2 | 9.6 RP 4.3/2.2 | 24.2 | 1.2 | 1.0 | 21.8 |
| 4(*) | 3.8 Y 5.5/1.2 | 5.7 YR 5.4/1.7 | 8.1 | 0.1 | 0.5 | 6.0 |

(*) : example not forming part of the invention.

These results show that the dye composition of Example 3 in accordance with the invention, that is to say one containing the combination of 2-n-propyl-para-phenylenediamine and 2-methyl-5-N-(β-hydroxyethyl)aminophenol in a coupler/base molar ratio equal to 10:1, gives the hair a much more intense coloration than the composition of Example 4 which does not form part of the invention since it contains this same combination but in a molar ratio equal to 107:1, and as described, for example in European patent application EP-A-0,634,163.

We claim:

1. A composition for the oxidation dyeing of keratin fibres comprising:

at least one oxidation base chosen from 2-n-propyl-para-phenylenediamine and acid addition salts thereof, at least one coupler chosen from the meta-aminophenols of formula (I) below, and acid addition salts thereof:

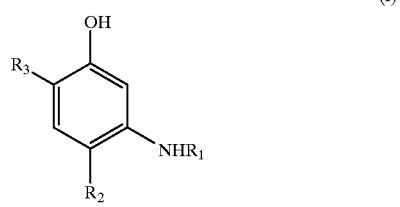

(I)

wherein:

$R_1$ is chosen from a hydrogen atom, $C_1$–$C_4$ alkyl radicals, $C_1$–$C_4$ monohydroxyalkyl radicals and $C_2$–$C_4$ polyhydroxyalkyl radicals, $R_2$ is chosen from a hydrogen atom, $C_1$–$C_4$ alkyl radicals, $C_1$–$C_4$ alkoxy radicals and a halogen atom chosen from chlorine, bromine and fluorine, $R_3$ is chosen from a hydrogen atom, $C_1$–$C_4$ alkyl radicals, $C_1$–$C_4$ alkoxy radicals, $C_1$–$C_4$ monohydroxyalkyl radicals, $C_2$–$C_4$ polyhydroxyalkyl radicals, $C_1$–$C_4$ monohydroxyalkoxy radicals and $C_2$–$C_4$ polyhydroxyalkoxy radicals, wherein said meta-aminophenols of formula (I) and acid addition salts thereof and said 2-n-propyl-para-phenylenediamine and acid addition salts thereof are present in a molar ratio of less than or equal to 10:1.

2. A composition according to claim 1 wherein said keratin fibres are human keratin fibres.

3. A composition according to claim 2 wherein said human keratin fibres are hair.

4. A composition according to claim 1 wherein the molar ratio of said meta-aminophenols of formula (I) and acid addition salts thereof/said 2-n-propyl-para-phenylenediamine and acid addition salts thereof is less than or equal to 5:1.

5. A composition according to claim 1 wherein said meta-aminophenols of formula (I) are chosen from meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol and 5-(γ-hydroxypropylamino)-2-methylphenol, and acid addition salts thereof.

6. A composition according to claim 1 wherein said acid addition salts are chosen from hydrochlorides, hydrobromides, sulphates and tartrates.

7. A composition according to claim 1 wherein said at least one oxidation base is present in an amount ranging from 0.0005 to 10% by weight relative to the total weight of the dye composition.

8. A composition according to claim 7 wherein said at least one oxidation base is present in an amount ranging from 0.05 to 7% by weight relative to the total weight of the dye composition.

9. A composition according to claim 1 wherein said at least one coupler is present in in amount ranging from 0.0001 to 5% by weight relative to the total weight of the dye composition.

10. A composition according to claim 9 wherein said at least one coupler is presentin an amount ranging from 0.005 to 3% by weight relative to the total weight of the dye composition.

11. A composition according to claim 1 which further comprises water.

12. A composition according to claim 11 which further comprises a mixture of water and at least one organic solvent chosen from $C_1$–$C_4$ lower alkanols, glycerol, glycols, glycol ethers, and aromatic alcohols.

13. A composition according to claim 1 wherein said composition has a pH ranging from 5 to 12.

14. A composition according to claim 1 further comprising at least one additional ingredient chosen from couplers and oxidation bases wherein said couplers and oxidation bases are different than those of claim 1.

15. A process for dyeing keratin fibres comprising applying to said fibres a dyeing composition and developing the colour at acidic, neutral or alkaline pH with an oxidizing agent, wherein said dyeing composition comprises:

at least one oxidation base chosen from 2-n-propyl-para-phenylenediamine and acid addition salts thereof, at least one coupler chosen from the meta-aminophenols of formula (I) below, and acid addition salts thereof:

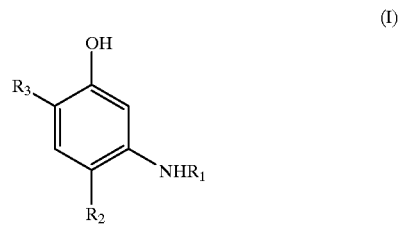

(I)

wherein:

$R_1$ is chosen from a hydrogen atom, $C_1$–$C_4$ alkyl radicals, $C_1$–$C_4$ monphydroxyalkyl radicals and $C_2$–$C_4$ polyhydroxyalkyl radicals.

$R_2$ is chosen from a hydrogen atom, $C_1$–$C_4$ alkyl radicals, $C_1$–$C_4$ alkoxy radicals and a halogen atom chosen from chlorine, bromine and fluorine, R₃ is chosen from a hydrogen atom, $C_1$–$C_4$ alkyl radicals, $C_1$–$C_4$ alkoxy radicals, $C_1$–$C_4$ monohydroxyalkyl radicals, $C_2$–$C_4$ polyhydroxyalkyl radicals, $C_1$–$C_4$ monohydroxyalkyl radicals and $C_2$–$C_4$ polyhydroxyalkyl radicals, wherein said meta-aminophenyls of formula (I) and acid addition salts thereof and said 2-n-propyl-para-phenylenediamine and acid addition salts thereof are present in a molar ratio of less than equal to 10:1.

16. A process according to claim 15 wherein said oxidizing agent is combined with said composition and immediately thereafter said composition and said oxidizing agent are applied to said fibres.

17. A process according to claim 15 wherein said oxidizing agent is combined with said composition after said composition is applied to said fibres.

18. A process according to claim 15 wherein said oxidizing agent is applied to said fibres and thereafter said composition is applied to said fibres.

19. A process according to claim 15 wherein said oxidizing agent and said composition are separately and simultaneously applied to said fibres.

20. A process according to claim 15 wherein said keratin fibres are human keratin fibres.

21. A process according to claim 20 wherein said human keratin fibres are hair.

22. A process according to claim 15 wherein said oxidizing agent is chosen from hydrogen peroxide, urea peroxide, alkali metal bromates and persalts.

23. A process according to claim 22 wherein said persalts are chosen from perborates and persulphates.

24. A multi-compartment dyeing kit comprising a first compartment containing a dye composition, and a second compartment comprising an oxidizing agent, wherein said dye compostion comprises;

at least one oxidation base chosen from 2-n-propyl-para-phenylenediamine and acid addition salts thereof, at least one coupler chosen from the meta-aminophenols of formula (I) below, and acid addition salts thereof:

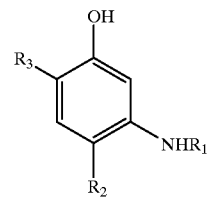

(I)

wherein:

$R_1$ is chosen from a hydrogen atom, $C_1$–$C_4$ alkyl radicals, $C_1$–$C_4$ monohydroxyalkyl radicals and $C_2$–$C_4$ polyhydroxyalkyl radicals, $R_2$ is chosen from a hydrogen atom, $C_1$–$C_4$ alkoxy radicals and a halogen atom chosen from chlorine, bromine and fluorine, $R_3$ is chosen from a hydrogen atom, $C_1$–$C_4$ alkyl radicals, $C_1$–$C_4$ alkoxy radicals, $C_1$–$C_4$ monohydroxyalkyl radicals, $C_2$–$C_4$ polyhydroxyalkyl radicals, $C_1$–$C_4$ monohydroxyalkoxy radicals and $C_2$–$C_4$ polyhydroxyalkoxy radicals, wherein said meta-aminophenols of formula (I) and acid addition salts thereof and said 2-n-propyl-para-phenylenediamine and acid addition salts thereof are present in a molar ratio less than or equal to 10:1.

* * * * *

UNITED STATES PATENT AND TRADEMARK OFFICE
CERTIFICATE OF CORRECTION

PATENT NO.: 6,001,136

DATED: December 14, 1999

INVENTOR(S): AUDOUSSET

It is certified that an error appears in the above-identified patent and that said Letters Patent is hereby corrected as shown below:

In claim 7, column 8, line 13, "ranqing" should read --ranging--.

In claim 10, column 8, line 25, "presentin" should read --present in--.

In claim 24, column 9, line 36, "comprises;" should read --comprises:--.

Signed and Sealed this

Eighth Day of August, 2000

Attest:

Q. TODD DICKINSON

Attesting Officer

Director of Patents and Trademarks